US006403579B1

(12) United States Patent
Heller

(10) Patent No.: US 6,403,579 B1
(45) Date of Patent: Jun. 11, 2002

(54) PHARMACEUTICAL COMPOSITIONS CONTAINING CARVEDILOL AND HYDROCHLOROTHIAZIDE

(75) Inventor: Rudolf Heller, Traunfeld (AT)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/447,872

(22) Filed: Nov. 23, 1999

(30) Foreign Application Priority Data

Nov. 27, 1998 (EP) ............................................ 98122489

(51) Int. Cl.⁷ ......................... A61K 31/54; A61K 31/40
(52) U.S. Cl. ..................... 514/223.5; 514/411
(58) Field of Search ............................... 514/411, 223.5

(56) References Cited

U.S. PATENT DOCUMENTS 5,019,398 A   5/1991   Daste
5,425,950 A   6/1995   Dandiker et al.

FOREIGN PATENT DOCUMENTS

| DE | 196 37 082 | 3/1998 |
| EP | 0004920 | 10/1979 |
| WO | WO 96/24348 | 8/1996 |
| WO | WO 98 05320 | 2/1998 |

OTHER PUBLICATIONS

Thoennes, C.J. and McCurdy, V.E., Drug Development and Industrial Pharmacy, 15, pp. 165–185 (1989).
Rhöm Pharma Weiterstat XP002145397 (1981).
Derwent Abstract for DE 196 37 082 (May 1998).
Widmann et al, Eur. J. Clinical Pharmacology 38(2) (1990) pp. 143–146.
von der Does et al, Eur. J. Clinical Pharmacology 382) (1990) pp. 147–152.
McTavish et al, Drugs 45(2) (1993) pp. 232–258.
Biston P. et al. Acta Cardiologica, 49, pp. 145–155 (1994).
Rudorf J.E. et al., Drugs, 36, Suppl 6, pp. 113–117 (1988).
Dupont A.G. et al., European Journal of Clinical Pharmacology, 38, Suppl 2, pp. S153–S157 (1990).
Widmann L. et al., European Journal of Clinical Pharmacology, 38, Suppl 2, pp. S143–S146 (1990).
A. Kleeemann et al., Pharmaceutically Active Substances; Syntheses, Patents, Uses, $2^{nd}$ Edition, Publisher: Georg Thieme, pp 469–470 (1982).

*Primary Examiner*—Raymond Henley, III
(74) *Attorney, Agent, or Firm*—George W. Johnston; John P. Parise

(57) ABSTRACT

A pharmaceutical combination preparation for the treatment of cardiac and cardiovascular disorders, such as hypertension, angina pectoris, cardiac insufficiency and illnesses associated therewith, contains the active substances carvedilol, or a pharmaceutically acceptable salt thereof, and hydrochlorothiazide, or a pharmaceutically acceptable salt thereof, as well as pharmaceutically usual additives.

9 Claims, No Drawings

PHARMACEUTICAL COMPOSITIONS CONTAINING CARVEDILOL AND HYDROCHLOROTHIAZIDE

BACKGROUND OF THE INVENTION

1. Field

The present invention is concerned with pharmaceutical combination preparations that are suitable for treating cardiac and cardiovascular disorders and the illnesses associated therewith. Specifically, the present invention relates to pharmaceutical combination preparations containing carvedilol and hydrochlorothiazide as active substances.

2. Description

Carvedilol, a compound of the formula:

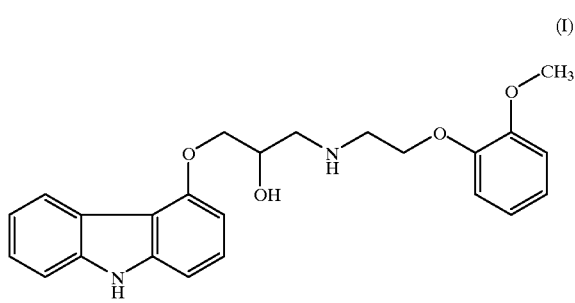

(I)

is a β-blocker with additional $\alpha_1$-blocking activity, which has been commercially available for several years under the trade name Coreg® in the United States and Dilatrend™ outside the United States.

Hydrochlorothiazide, a compound of the formula:

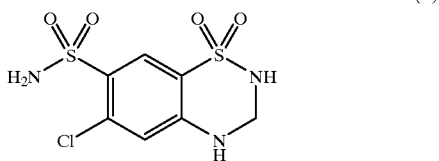

(II)

is a diuretic, which has been marketed for decades.

The combination of a β-blocker with a diuretic has been used successfully for treating cardiac and circulatory disorders such as hypertension, angina pectoris, cardiac insufficiency and illnesses associated therewith. Many studies have investigated the advantages of combination therapy using carvedilol and hydrochlorothiazide (e.g. Widmann et al., 1990, Eur J Clin Pharmacol 38(2):143–146; van der Does et al., 1990, Eur J Clin Pharmacol 38(2):147–152; McTavish et al., 1993, Drugs 45(2): 232–258). In all of these studies, the two active substances carvedilol and hydrochlorothiazide were sequentially administered in the form of individual tablets. A fixed combination of the two active substances could not be realized until the present invention.

A combined product was not earlier developed because the two active substances, carvedilol and hydrochlorothiazide, have different solubilities and, when granulated together, gave end products with inadequate active substance release and bioavailability. Thus, it was problematic to provide the two active substances as a combination preparation, such as a tablet. An object of the invention is to provide a solution to these problems.

SUMMARY OF THE INVENTION

The subject invention provides a pharmaceutical combination preparation containing the active substances (i) carvedilol, or a pharmaceutically acceptable salt thereof, and (ii) hydrochlorothiazide, or a pharmaceutically acceptable salt thereof, and at least one pharmaceutically acceptable additive.

The preferred weight ratio of (i) hydrochlorothiazide, or a pharmaceutically acceptable salt thereof, to (ii) carvedilol, or a pharmaceutically acceptable salt thereof, is between about 1:0.5 and about 1:10. Typically, the preparation is in dosage form containing (i) about 10 mg to about 50 mg of carvedilol, or a pharmaceutically acceptable salt thereof, and (ii) about 5 mg to about 30 mg of hydrochlorothiazide, or a pharmaceutically acceptable salt thereof. The acceptable additive includes binders, disintegrants, glidants, adsorption agents, separating agents, fillers, and carriers. A more preferred pharmaceutical combination preparation contains about 0 weight % to about 50 weight % lactose, about 0 weight % to about 50 weight % saccharose, about 0 weight % to about 10 weight % magnesium stearate, about 0 weight % to about 30 weight % cellulose, about 0 weight % to about 10 weight % polyvinylpyrrolidone, about 0 weight to about 10 weight % polymeric cellulose compounds, about 0 weight % to about 10 weight % highly dispersed silicon dioxide and about 0 weight % to about 20 weight % cross-linked polyvinylpyrrolidone. Most preferably, the preparation is in solid dosage form.

The subject invention also provides method for treating of cardiac and circulatory disorders which comprises administering an effective amount of a pharmaceutical combination preparation in dosage form containing the active substances (i) carvedilol, or a pharmaceutically acceptable salt thereof, and (ii) hydrochlorothiazide, or a pharmaceutically acceptable salt thereof, and at least one pharmaceutically acceptable additive.

Another aspect of the subject invention is a process for producing a solid dosage form pharmaceutical combination preparation containing carvedilol, or a pharmaceutically acceptable salt thereof, and hydrochlorothiazide, or a pharmaceutically acceptable salt thereof. The process comprises (i) forming a press mass containing a carvedilol, or pharmaceutically acceptable salt thereof, granulate and a hydrochlorothiazide carvedilol, or pharmaceutically acceptable salt thereof, granulate and (ii) compressing the press mass to form the solid dosage form pharmaceutical combination preparation. The two granulates each having a granulate moisture content between about 6% and about 20% and a bulk density between about 0.1 g/ml and about 1.5 g/ml. The granuate moisture content and the bulk density of the two granulates do not vary from each other by more than about 30%.

The granulate moisture content of the carvedilol, or pharmaceutically acceptable salt thereof, granulate and the hydrochlorothiazide, or pharmaceutically acceptable salt thereof, granulate is preferably between about 10% and about 15%. The bulk density of both the carvedilol, or pharmaceutically acceptable salt thereof, granulate and the hydrochlorothiazide, or pharmaceutically acceptable salt thereof, granulate is preferably between about 0.4 g/ml and about 0.75 g/ml. Compressing is generally accomplished using a tablet press to form tablets. The process can further comprise coating the solid dosage form with a pharmaceutically acceptable aqueous film suspension. The coating of the solid dosage form is typically first performed at a rate of about 30 g to about 50 g of film suspension per minute during the first about 30 minutes to about 70 minutes and then performed at a rate of about 60 g to about 90 g of film suspension per minute until the film coating has finished. Pharmaceutically acceptable solid dosage form combination preparations prepared using the described process are also part of the invention. The amount of the disintegrant in the dosage form is typically at least 5 weight %.

Another aspect of the invention is a light-protecting film suspension for use in coating solid dosage form pharmaceutical preparations. This light-protecting film preferably comprises: about 10 weight % to about 50 weight % poly(ethyl acrylate, methyl acrylate) 2:1, 800,000; about 1 weight % to about 10 weight % sodium citrate; about 1 weight % to about 25 weight % methylhydroxypropylcellulose; about 0 weight % to about 20 weight % macrogol 10,000; about 5 weight % to about 40 weight % talc; about 2 weight % to about 25 weight % titanium dioxide; about 0 weight % to about 10 weight % indigocarmine color lacquer; about 0 weight % to about 2 weight % polysorbate; and about 0 weight % to about 1.0 weight % dimethicone.

DETAILED DESCRIPTION OF THE INVENTION

The present invention will now be described in terms of its preferred embodiments. These embodiments are set forth to aid in understanding the invention but are not to be considered limiting.

The present invention is concerned with pharmaceutical combination preparations containing the active substances carvedilol, or a pharmaceutically acceptable salt thereof, and hydrochlorothiazide, or a pharmaceutically acceptable salt thereof, as well as pharmaceutically usual additives. Moreover, the present invention is concerned with the use of this combination preparation for the treatment of cardiac and circulatory disorders such as hypertension, angina pectoris, cardiac insufficiency and illnesses associated therewith.

The term "pharmaceutical combination preparation" refers to a pharmaceutically acceptable dosage form which simultaneously contains two or more active substances.

Pharmaceutically acceptable salts of the compounds of the formulas (I) and (II) include alkali salts, such as Na or K salts, alkaline earth metal salts, such as Ca and Mg salts, as well as salts with organic or inorganic acids, such as, for example, hydrochloric acid, hydrobromic acid, nitric acid, sulphuric acid, phosphoric acid, citric acid, formic acid, maleic acid, acetic acid, succinic acid, tartaric acid, methanesulphonic acid or toluenesulphonic acid, which are non-toxic for living organisms.

The phrase "drying loss" of granulates refers to the gravimetric determination of the weight difference between original granulate and the granulate dried to constant weight. Drying can be effected, for example, in a drying oven at elevated temperatures, with an infrared lamp, with a microwave apparatus, with a hot air blower, etc.

Measurement of the granulate moisture in the present specification was effected with a SUPERMATIC rapid hygrometer from the firm Foss Electric (accuracy ±0.25%). The measurement principle is based on the measurement of the dielectric constants of the measured material. A sample amount of 250 g was used.

In a preferred embodiment of the combination preparation in accordance with the invention the weight ratio of hydrochlorothiazide or a pharmaceutically acceptable salt thereof to carvedilol or a pharmaceutically acceptable salt thereof lies between 1:0.5 and 1:10, preferably between 1:0.5 and 1:5, especially at 1:2.

A preferred combination preparation in accordance with the invention contains between 10 mg and 50 mg, preferably 25 mg, of carvedilol or a pharmaceutically acceptable salt thereof and between 5 mg and 30 mg, preferably 12.5 mg, of hydrochlorothiazide or a pharmaceutically acceptable salt thereof in an oral dosage form.

The combination preparations in accordance with the invention may contain additives such as binders, plasticizers, diluents, carriers, glidants, antistatics, adsorbing agents, separating agents, dispersants, drageeing lacquers, de-foamers, film formers, emulsifiers, disintegrants and fillers in the tablets and/or the coating. Tablets or granulates, for example, can contain flavor-improving additives as well as substances usually used as preservatives, stabilizers, moisture-retainers and emulsifiers, salts for varying the osmotic pressure, buffers and other additives.

The additives mentioned above can comprise organic or inorganic substances, e.g. water, sugar, salts, acids, bases, alcohols, organic polymeric compounds, and the like. Lactose, saccharose, magnesium stearate, various celluloses and substituted celluloses, polymeric cellulose compounds, highly dispersed silicon dioxide, maize starch, talc and various polymeric polyvinylpyrrolidone compounds are preferred additives. For example, polyvinylpyrrolidones, which are not cross-linked, with a molecular weight of 8,000 to 630,000, preferably 25,000, and cross-linked polyvinylpyrrolidones with a molecular weight greater than 1,000,000 can be used. It is a prerequisite that all additives used in the production are non-toxic and advantageously do not alter the bioavailability of the active substances.

Solid dosage forms which contain about 0–50 weight % lactose, about 0–50 weight % saccharose, about 0–10 weight % magnesium stearate, about 0–30 weight % cellulose, about 0–10 weight % polyvinylpyrrolidone, about 0–10 weight % polymeric cellulose compounds, about 0–10 weight % highly dispersed silicon dioxide, and about 0–20 weight % cross-linked polyvinylpyrrolidone as additives are especially preferred.

A combination preparation in accordance with the invention which contains about 25 mg of carvedilol, about 12.5 mg of hydrochlorothiazide, about 25.0 mg of saccharose, about 28.06 mg of lactose, about 1.78 mg of polyvinylpyrrolidone, about 20.17 mg of cross-linked polyvinylpyrrolidone, about 10–0 mg of microcrystalline cellulose, about 5.32 mg of highyl dispersed silicon dioxide and about 2.17 mg of magnesium stearate per 130 mg solid dosage form is especially preferred.

Further, it has surprisingly been found that the process used for the production of the combination preparations permits the two active substance granulates to be pressed to a stable tablet in one operation.

The active substances and additives required for the production of the combination preparation in accordance with the invention are known (Carvedilol: EP 0004920; hydrochlorothiazide: Pharmaceutically Active Substances; Syntheses, Patents, Uses, A. Kleemann et al., $2^{nd}$ Edition, published by Georg Thieme, 1982, page 469) or are commercially available or can be produced in accordance with known methods.

The process for the production of the combination preparation in accordance with the invention can comprise the steps described hereinafter, but is not limited to these individual steps:

a) the production of a carvedilol granulate;
b) the production of a hydrochlorothiazide granulate;
c) the processing of a carvedilol granulate and a hydrochlorothiazide granulate to a press mass, with the two granulates each having a granulate moisture content between 6 and 20% and a bulk density between 0.1 and 1.5 g/ml and the granuate moisture content and the bulk density of the two granulates in each case not varying from one another by more than 30%, preferably 20%;

d) the production of a solid dosage form, preferably a tablet, from the press mass obtained under c).

The carvedilol granulate is preferably produced by fluidized bed granulation, the hydrochlorothiazide granulate preferably by granulation in a high speed mixer-granulator (e.g. DIOSNA P 450).

The granulate moisture content of the carvedilol granulate and of the hydrochloro-thiazide granulate preferably lies between 10 and 15%.

The bulk density of the two granulates preferably lies between 0.4 and 0.75 g/ml.

In a particular embodiment the combination peparation, as well as a carvedilol preparation alone, can be provided with a light-protecting film.

As carvedilol is an active substance which is particularly sensitive to light, a distinct brown coloration of the active substance can occur not only in the case of the pure active substance but also in the case of carvedilol-containing medicaments in different dosages when these forms are exposed to light.

Under a "light-protecting film" there is to be understood a coating based on an aqueous film suspension applied to the dosage form, preferably by spraying.

The film suspension preferably contains about 10–50 weight % poly(ethyl acrylate, methyl acrylate) 2:1, 800,000, about 1–10 weight % sodium citrate, about 1–25 weight % methylhydroxypropylcellulose, about 0–20 weight % macrogol 10,000, about 5–40 weight % talc, about 2–25 weight % titanium dioxide, about 0–10 weight % indigocarmine color lacquer, about 0–2 weight % polysorbate and about 0–1.0 weight % dimethicone.

A light-protecting film which contains about 2.348 mg of poly(ethyl acrylate, methyl acrylate) 2:1, 800,000, about 0.308 mg of sodium citrate, about 1.018 mg of methylhydroxypropylcellulose, about 0.644 mg of macrogol 10,000, about 1.624 mg of talc, about 0.950 mg of titanium dioxide, about 0.170 mg of indigocarmine color lacquer, about 0.034 mg of polysorbate and about 0.004 mg of dimethicone per 7 g of film suspension is especially preferred.

All polysorbates (polyoxyethylene derivatives) of the polysorbate 20 to polysorbate 85 type, preferably polysorbate 80, can be used for the film coating.

Although the light-protecting film described above is used for the film coating of oral dosage forms, such as e.g. tablets, containing carvedilol, not only as a single but also as a combination preparation, it is, of course, also suitable for tablets containing other light-sensitive active substances.

In a further embodiment the invention also includes a process for the application of a light-protecting film.

Since carvedilol is not very water soluble, carvedilol-containing medicaments typically contain an especially high content of disintegrant (15–20 weight % cross-linked polyvinylpyrrolidone). It is known to the skilled artisan that the direct application of an aqueous suspension to a tablet with a disintegrant content of more than 5 weight % in one operation is typically associated with problems because a reaction can occur between water from the film suspension and disintegrant from the tablet, which softens the surface of the tablet. It has now surprisingly been found that by the inventive process described below, an aqueous suspension, preferably an aqueous light-protecting suspension, such as the aforementioned film suspension, can be applied in one operation to a tablet having a disintegrant content of more than 5%.

The specific procedure at the beginning of the film coating is critical for the process: The spray rate must be so low at the beginning on the one hand to permit the formation of a film on the tablet surface and on the other hand to remove the water of the film suspension as rapidly as possible from the tablet surface. This procedure is additionally assisted by the supply of large amounts of air and a high air supply temperature in the drageeing kettle. As soon as this critical phase of the film coating has been completed, i.e. a thin film has formed over the entire tablet, the spray rate can be increased to an extent which is usual in the case of conventional film coatings. The film coating can be carried out to the end using this increased spray rate. The aforementioned inventive film coating procedure is also facilitated and assisted by the composition of the film suspension.

The tablets to be film coated are added to a drageeing kettle (e.g. a 50 kg drageeing kettle from the firm BRUCKS, Model XI) and film coated with the light-protecting suspension (film coating e.g. with a binary spray nozzle from the firm WALTHER, PILOT type, Model WA).

The following data refer to a film coating using the aforementioned drageeing kettle and binary spray nozzles. However, these values can be readily varied by the artisan depending on the equipment used.

During the first 30 to 70, preferably 50, minutes the film coating of the solid dosage form is effected with 30 to 50 g, preferably with 40 g, of film suspension per minute and subsequently until the film coating has finished with 60 to 90 g, preferably with 74 g, of film suspension per minute. In a process variant, after 40 to 60 minutes, the spray rate can also be increased continuously to the maximum value of 60 to 90 g per minute.

The film coating process described above can be used for the film coating of any pharmaceutically acceptable solid dosage form, such as tablets, with a disintegrant content of more than 5%. Thus, for example, a pharmaceutically acceptable solid dosage form containing 0–20 weight % carvedilol, 0–50 weight % lactose, 0–50 weight % saccharose, 0–10 weight magnesium stearate, 0–30 weight cellulose, 0–10 weight polyvinylpyrrolidone, 0–10 weight highly dispersed silicon dioxide and 0–20 weight cross-linked polyvinyl-pyrrolidone can also be coated with a pharmaceutically acceptable aqueous film suspension. The combination preparations produced and film coated according to the process in accordance with the invention have a surprisingly long stability.

Oral administration is the preferred form of administration for the combination preparation in accordance with the invention. Preferred dosage forms include tablets, capsules and dragees. However, tablets are most preferred. The dosage in which the combination preparation in accordance with the invention is administered depends on the age and the requirements of the patient and on the route of administration. In general, dosages of about 10–50 mg of carvedilol and about 5–30 mg of hydrochlorothiazide per day come into consideration.

The following Examples are intended to illustrate the preferred embodiments of the present invention, without limiting them.

EXAMPLE 1

Production of a carvedilol granulate a) Production of the suspension 64,500 g of purified water are placed in a kettle and 15,000 g of sieved lactose D80, 7,500 g of sieved saccharose and 1,500 g of polyvinylpyrrolidone 25,000 (e.g. Kollidon 25) are added thereto and dissolved while stirring for 30 minutes. Subsequently, 3,000 g of highly dispersed silicon dioxide (e.g. Aerosil 200) and 37,500 g of finely crystalline carvedilol are added to the above solution and stirred for 30 minutes until a homogeneous suspension is produced. The suspension is pumped over a colloid mill and a hand sieve into a different container. The suspension is stirred continuously until the fluidized bed granulation has finished in order to prevent settling.

b) Fluidized bed granulation 30,000 g of finely ground saccharose and 15,000 g of cross-linked polyvinylpyrrolidone (e.g. Plasdone XL) are placed in the pan of the fluidized bed granulator (e.g. GLATT - WSG 150). The suspension obtained under a) is introduced using a tube pump (internal tube diameter: 10 mm) via a 2.2 mm binary nozzle ($1^{st}$ material: suspension; $2^{nd}$ material: purified compressed air of 6 bar). The spray granulation takes place with an air supply temperature of about 80° C. and a product temperature of about 34° C. to 37° C. The moisture content of the spent air amounts to 50 to 70% of the relative humidity, the spraying time amounts to about 120 minutes.

c) Sieving

After the fluidized bed granulation the granulate is passed through a sieve with a mesh size of 1.2 mm.

d) Final mixing 8,250 g of cross-linked polyvinylpyrrolidone (e.g. Plasdone XL) and 3,000 g of highly dispersed silicon dioxide (e.g. Aerosil 200) are passed through a sieve with a mesh size of 1.2 mm and homogenized with the granulate in a mixer (e.g. a plowshare mixer from the firm LÖDIGE. Then, 2,250 g of magnesium stearate are passed through a sieve with a mesh size of 1.2 mm and the sieved magnesium stearate is mixed briefly with the granulate and the granulate yield is established (target weight: 123,000 g). Subsequently, the IPC values (IPC=in process control) of the final mixture are determined, with it being necessary to achieve the following target values:

| Granulate moisture | 11.5–12.5% |
|---|---|
| Drying loss (microwave) | 2.0–3.0% |
| Bulk density | 0.50–0.65 g/ml |

EXAMPLE 2

Production of a hydrochlorothiazide granulate a) Production of the granulation solution 1,040 g of polyvinylpyrrolidone 25,000 (e.g. Kollidon 25 having a mean average mol wt of approximately 25,000) are dissolved in 9,620 g of water while stirring.

b) Granulation of the active substance and additives 19,500 g of hydrochlorothiazide and 28,340 g of lactose are mixed in a mixer-granulator (e.g. DIOSNA) for 4 minutes. Thereafter, 10,660 g of the granulation solution from a) are sprayed into the mixer with a spray pressure of 2 bar and granulated in the mixer-granulator for 5 minutes. The mist granulate is dried to a defined final moisture content at an air inlet temperature of 75° C.

c) Granulate sieving

The dried granulate from b) is passed through a pharma sieve with a mesh size of 1.25 mm [and] subsequently the granulate moisture is determined. The target value lies at 9.5 to 11.0%. Subsequently, the granulate weight is determined (target weight: 74,880 g).

d) Production of the final mixture 15,600 g of microcrystalline cellulose together with 7,280 g of cross-linked polyvinylpyrrolidone (e.g. Plasdone XL), 2,080 g of highly dispersed silicon dioxide (e.g. Aerosil 200) and 1,040 g of magnesium stearate are passed through a pharma sieve with a mesh size of 1.25 mm. This sieved material and the sieved granulate from c) are added to a pharma mixer and mixed for 30 seconds. The finished mixture is discharged into a pharma container and the yield is determined. Subsequently, the IPC values of the final mixture are determined, with it being necessary to achieve the following target values:

| Granulate moisture | 10.0–11.0% |
|---|---|
| Drying loss (microwave) | 1.5–2.5% |
| Bulk density | 0.50–0.65 g/ml |

EXAMPLE 3

Production of a carvedilol-hydrochlorothiazide press mass a) Mixing of the press mass 70,340 g of hydrochlorothiazide granulate and 120,160 g of carvedilol granulate are placed in a suitable pharma mixer (e.g. plowshare mixer LÖDIGE) and homogeneously mixed. The mixing time amounts to 3 minutes. The finished mixture is filled into an air-tight container through which light cannot pass and the yield is determined (target weight: 19,500 g). Subsequently, the IPC values of the final mixture are determined, with it being necessary to achieve the following target values:

| Granulate moisture | 11.0–12.0% |
|---|---|
| Drying loss (microwave) | 2.0–3.0% |
| Bulk density | 0.50–0.65 g/ml |

EXAMPLE 4

Production of the tablets

The press mass is pressed using a computer-controlled high performance rotary tablet press (e.g. KILIAN TX 40 with automatic pressing force control as well as regulation and control of the tablet weight) to tablets, which are stored in container through which light cannot pass.

EXAMPLE 5

Protection of carvedilol-containing medicaments from light by film coating a) Production of the film suspension:

364 g of Pharmacoat (=methylhydroxypropylcellulose), 230 g of macrogol 10,000 (polyethylene glycol, approximate average mol wt of 10,000), 110 g of sodium citrate, 979 g of talc, 339 g of titanium dioxide, 12 g of Tween (polysorbate 80), 61 g of indigocarmine color lacquer and 4 g of dimethicone are dissolved in 6,900 g of hot water (30–60° C.) while stirring. The homogeneous solution is passed twice through a colloid mill. 401 g of Eudragit NE 30 D are added immediately before the film coating.

b) Film coating:

60–70 kg of dust-free tablets from Example 3 are placed in a drageeing kettle and film coated with the suspension from a). The cores are sprayed from above, with the distance of the spray nozzle from the core bed being about 60–70 cm. A binary nozzle (compressed air/liquid) with a diameter of 1.8 mm is used for this purpose. The sprayed air pressure (purified compressed air) amounts to 3 bar, the temperature of the input air amounts to 70° C., the amount of input air amounts to 350–500 m³/h and the amount of spent air amounts to 700–1,000 m³/h. A tube pump is used to introduce the liquid, with the PVC pipe having an external diameter of 8 mm and an internal diameter of 4 mm. The pump speed is 10 rpm during the first 50 minutes and is subsequently 25 rpm. Based on the film suspension, the pump speed is 40 g suspension/minute during the first 50 minutes and subsequently (about a further 100 minutes) it is increased stepwise up to 74 g suspension/minute. The rotation velocity of the kettle is 12 rpm during the first 50 minutes and is thereafter 18 rpm. The kettle inclination lies at 60 degrees.

EXAMPLE A

Tablets containing the following ingredients can be produced according to the process described above:

| Active substances | |
| --- | --- |
| Carvedilol | 25.000 mg |
| Hydrochlorothiazide | 12.500 mg |
| Additives | |
| Saccharose Ph. Eur. | 25.000 mg |
| Lactose 1 H$_2$O Ph. Eur. | 28.060 mg |
| Polyvinylpyrrolidone 25,000 Ph. Eur. | 1.780 mg |
| Cross-linked polyvinylpyrrolidone NF | 20.170 mg |
| Microcrystalline cellulose Ph. Eur. | 10.000 mg |
| Highly dispersed silicon dioxide Ph. Eur. | 5.320 mg |
| Magnesium stearate Ph. Eur. | 2.170 mg |
| Film coating | |
| Poly(ethyl acrylate, methyl acrylate) 2:1, 800,000 average mol wt | 2.248 mg |
| Sodium citrate Ph. Eur. | 0.308 mg |
| Methylhydroxypropylcellulose Ph. Eur. | 1.018 mg |
| Macrogol 10,000 | 0.644 mg |
| Talc Ph. Eur. | 1.624 mg |
| Titanium dioxide Ph. Eur. | 0.950 mg |
| Indigocarmine color lacquer | 0.170 mg |
| Polysorbate 80 Ph. Eur. | 0.034 mg |
| Dimethicone | 0.004 mg |

Upon reading the present specification, various alternative embodiments will become obvious to the skilled artisan. These embodiments are to be considered within the scope and spirit of the invention, which is only to be limited by the claims that follow and their equivalents.

What is claimed is:

1. A process for producing a solid dosage form pharmaceutical combination preparation containing carvedilol, or a pharmaceutically acceptable salt thereof, and hydrochlorothiazide, or a pharmaceutically acceptable salt thereof, which comprises:

a) forming a press mass containing a carvedilol, or pharmaceutically acceptable salt thereof, granulate and a hydrochlorothiazide carvedilol, or pharmaceutically acceptable salt thereof, granulate, the two granulates each having a granulate moisture content between about 6% and about 20% and a bulk density between about 0.1 g/ml and about 1.5 g/ml, the granuate moisture content and the bulk density of the two granulates not varying from each other by more than about 30%; and b) compressing the press mass to form the solid dosage form pharmaceutical combination preparation.

2. The process according to claim 1, wherein the granulate moisture content of the carvedilol, or pharmaceutically acceptable salt thereof, granulate and the hydrochlorothiazide, or pharmaceutically acceptable salt thereof, granulate is between about 10% and about 15%.

3. The process according to claim 1, wherein the bulk density of both the carvedilol, or pharmaceutically acceptable salt thereof, granulate and the hydrochlorothiazide, or pharmaceutically acceptable salt thereof, granulate is between about 0.4 g/ml and about 0.75 g/ml.

4. The process according to claim 1, wherein the compressing is performed using a tablet press to form tablets.

5. The process according to claim 1 further comprises coating the solid dosage form with a pharmaceutically acceptable aqueous film suspension.

6. The process according to claim 5, wherein the film coating of the solid dosage form is first performed at a rate of about 30 g to about 50 g of film suspension per minute during the first about 30 minutes to about 70 minutes and then performed at a rate of about 60 g to about 90 g of film suspension per minute until the film coating has finished.

7. A pharmaceutically acceptable solid dosage form combination preparation containing carvedilol, or a pharmaceutically acceptable salt thereof, and hydrochlorothiazide, or a pharmaceutically acceptable salt thereof, prepared by a process that comprises:

a) forming a press mass containing a carvedilol, or pharmaceutically acceptable salt thereof, granulate and a hydrochlorothiazide carvedilol, or pharmaceutically acceptable salt thereof, granulate, the two granulates each having a granulate moisture content between about 6% and about 20% and a bulk density between about 0.1 g/ml and about 1.5 g/ml, the granuate moisture content and the bulk density of the two granulates not varying from each other by more than about 30%; and b) compressing the press mass to form the solid dosage form pharmaceutical combination preparation.

8. The pharmaceutically acceptable solid dosage form according to claim 7, wherein the amount of disintegrant in the dosage form is at least 5 weight %.

9. A light-protecting film suspension for use in coating solid dosage form pharmaceutical preparations, which comprises: about 10 weight % to about 50 weight % poly(ethyl acrylate, methyl acrylate) 2:1, 800,000; about 1 weight % to about 10 weight % sodium citrate; about 1 weight % to about 25 weight % methylhydroxypropylcellulose; about 0 weight % to about 20 weight % macrogol 10,000; about 5 weight % to about 40 weight % talc; about 2 weight % to about 25 weight % titanium dioxide; about 0 weight % to about 10 weight % indigocarmine color lacquer; about 0 weight % to about 2 weight % polysorbate; and about 0 weight % to about 1.0 weight % dimethicone.

* * * * *